(12) United States Patent
Chien et al.

(10) Patent No.: US 6,960,155 B2
(45) Date of Patent: Nov. 1, 2005

(54) CYCLING-TYPE PHYSICAL THERAPY APPARATUS WITH AN ELECTRICAL STIMULATION DEVICE

(75) Inventors: Chih-Da Chien, Kaohsiung (TW); Po-Hsing Lee, Taipei Hsien (TW)

(73) Assignee: ZMI Electronics Ltd., Kaohsiung (TW)

(*) Notice: Subject to any disclaimer, the term of this patent is extended or adjusted under 35 U.S.C. 154(b) by 188 days.

(21) Appl. No.: 10/464,183

(22) Filed: Jun. 18, 2003

(65) Prior Publication Data

US 2004/0259693 A1 Dec. 23, 2004

(51) Int. Cl.$^7$ .............................................. A63B 21/00
(52) U.S. Cl. ...................................................... 482/62
(58) Field of Search ........................... 482/1–9, 51, 54, 482/57, 61, 62, 900–902

(56) References Cited

U.S. PATENT DOCUMENTS 4,717,146 A * 1/1988 Nohara ......................... 482/62
4,947,836 A * 8/1990 Laenger et al. ............... 607/48

* cited by examiner

Primary Examiner—Glenn E. Richman
(74) Attorney, Agent, or Firm—Ohlandt, Greeley, Ruggiero & Perle, L.L.P.

(57) ABSTRACT

A cycling-type physical therapy apparatus includes a foot-operated pedal mechanism, a hand-operated assist mechanism, a transmission mechanism, and an electrical stimulation device, all of which are mounted on a frame assembly. The transmission mechanism is coupled to the pedal mechanism and the assist mechanism for transmitting auxiliary drive power applied through the assist mechanism to the pedal mechanism. The electrical stimulation device is operable so as to generate electrical stimulus for muscle stimulation of the user of the apparatus.

21 Claims, 8 Drawing Sheets

CYCLING-TYPE PHYSICAL THERAPY APPARATUS WITH AN ELECTRICAL STIMULATION DEVICE

BACKGROUND OF THE INVENTION

1. Field of the Invention

The invention relates to a physical therapy apparatus, more particularly to a cycling-type physical therapy apparatus with an electrical stimulation device.

2. Description of the Related Art

Referring to FIG. 1, a conventional cycling-type physical therapy apparatus 1 is shown to include a frame assembly 11, a seat member 12, a foot-operated pedal mechanism 13, and an electrical stimulation device 14. The seat member 12 is mounted on a rear part of the frame assembly 11. The pedal mechanism 13 is mounted on a front part of the frame assembly 11 and is operable for lower limb exercise of the patient seated on the seat member 12. The stimulation device 14 is mounted on the frame assembly 11 and is provided with a set of electrical probes 141. When operated, the stimulation device 14 generates electrical stimulus for muscle stimulation of a patient on the seat member 12.

Although the conventional physical therapy apparatus 1 achieves its intended purpose, it is not adjustable to suit various physical sizes of patients, which can diminish the effectiveness of the exercise performed by the patient. Moreover, since patients are required to be carried and transferred from a wheelchair to the seat member 12, inconveniences to both the patient and an attendant of the patient arise. Further, the conventional apparatus 1 lacks an assist mechanism that can aid patients who experience difficulty in operating the pedal mechanism 13.

SUMMARY OF THE INVENTION

Therefore, the object of the present invention is to provide a cycling-type physical therapy apparatus that is capable of overcoming the aforesaid drawbacks of the prior art.

According to one aspect of the present invention, a cycling-type physical therapy apparatus comprises a frame assembly, a foot-operated pedal mechanism, a hand-operated assist mechanism, a transmission mechanism, and an electrical stimulation device. The pedal mechanism, the assist mechanism, the transmission mechanism, and the stimulation device are mounted on the frame assembly. The transmission mechanism is coupled to the pedal mechanism and the assist mechanism for transmitting auxiliary drive power applied through the assist mechanism to the pedal mechanism. The stimulation device is operable so as to generate electrical stimulus for muscle stimulation.

According to another aspect of the present invention, a cycling-type physical therapy apparatus comprises a frame assembly, a foot-operated pedal mechanism, an adjustable mechanism, and an electrical stimulation device. The frame assembly includes a base member and a post member. The base member has a front end and a rear end opposite to the front end in a first direction. The post member includes a first post section having a lower end mounted on the front end of the base member, and an upper end opposite to the lower end in a second direction transverse to the first direction. The post member further includes a second post section having a lower end coupled to the upper end of the first post section and pivotable about a first pivot axis that extends in a third direction transverse to the first and second directions. The second post section further has an upper end opposite to the lower end of the second post section in the second direction. The pedal mechanism is mounted on the second post section. The adjustable mechanism serves for adjusting inclination of the second post section relative to the base member. The electrical stimulation device is mounted on the frame assembly and is operable so as to generate electrical stimulus for muscle stimulation. The rear end of the base member is configured to permit movement of the wheelchair thereabove in the first direction toward the post member, and the adjustable mechanism permits adjustment of the second post section so that the patient can tread on the pedal mechanism while seated on the wheelchair.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 2:
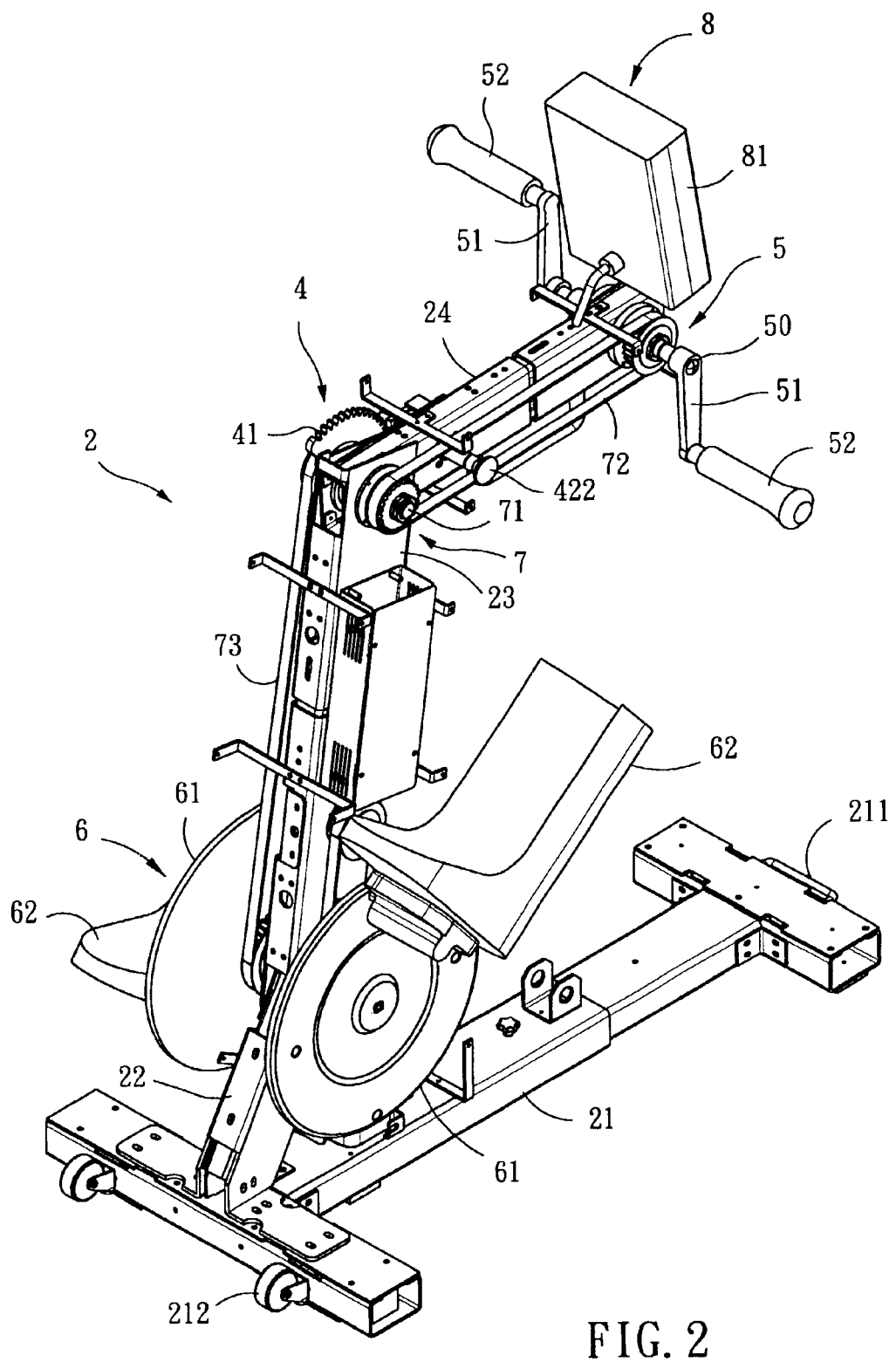
FIG. 2 is a perspective view of the preferred embodiment of a cycling-type physical therapy apparatus according to the present invention.
Figure 3:
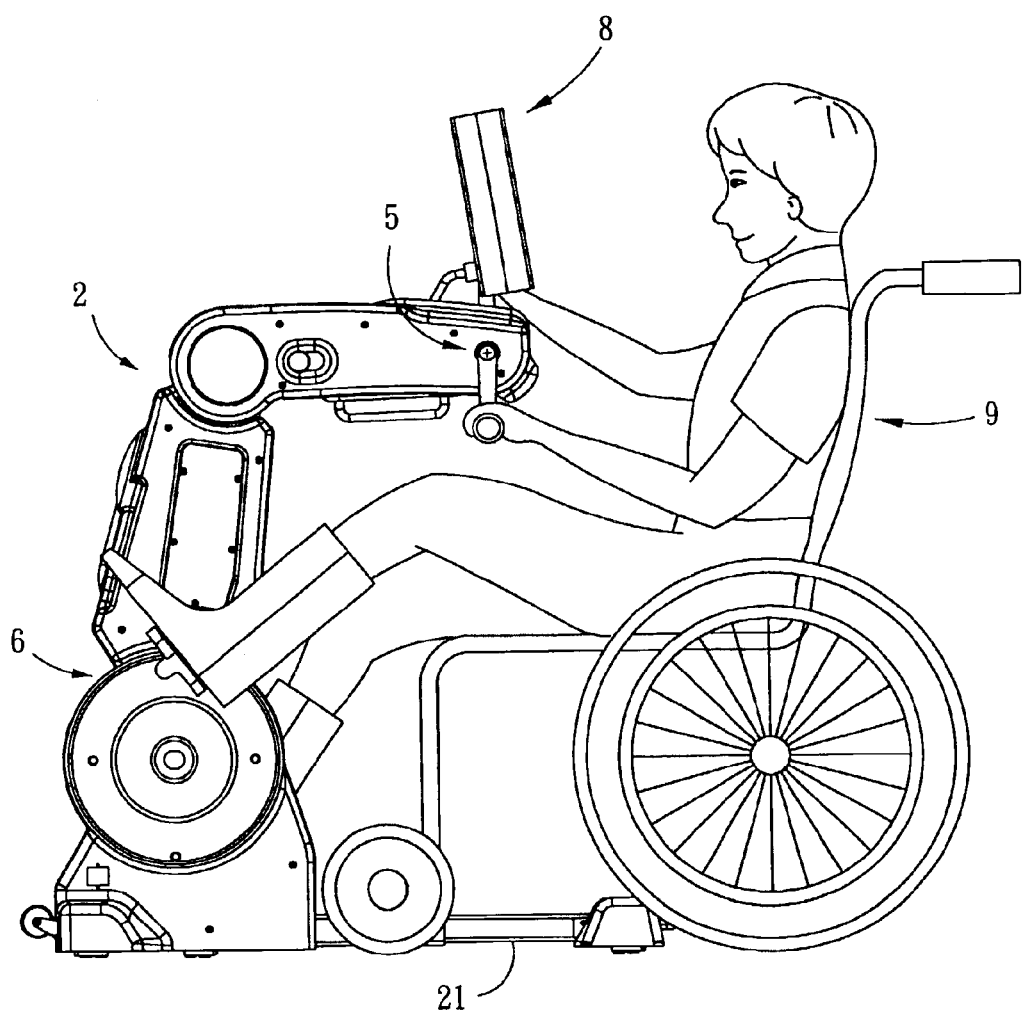
FIG. 3 is a schematic view of the preferred embodiment in a state of use.

Referring to FIGS. 2 and 3, the preferred embodiment of a cycling-type physical therapy apparatus according to this invention is shown to include a frame assembly 2, a foot-operated pedal mechanism 6, a hand-operated assist mechanism 5, a transmission mechanism 7, and an electrical stimulation device 8.

The physical therapy apparatus is adapted for use by a physically impaired patient seated on a wheelchair 9.

The frame assembly 2 includes a base member 21 and a post member. The base member 21 has a front end and a rear end opposite to the front end in a first direction. A wheel unit 212 and a handle unit 211 are mounted on the front and rear ends of the base member 21, respectively. When it is desired to move the physical therapy apparatus from one location to another, the physical therapy apparatus is pulled at the handle unit 211 such that the rear end of the base member 21 is lifted from the ground and such that the wheel unit 212 can roll on the ground.

Figure 4:
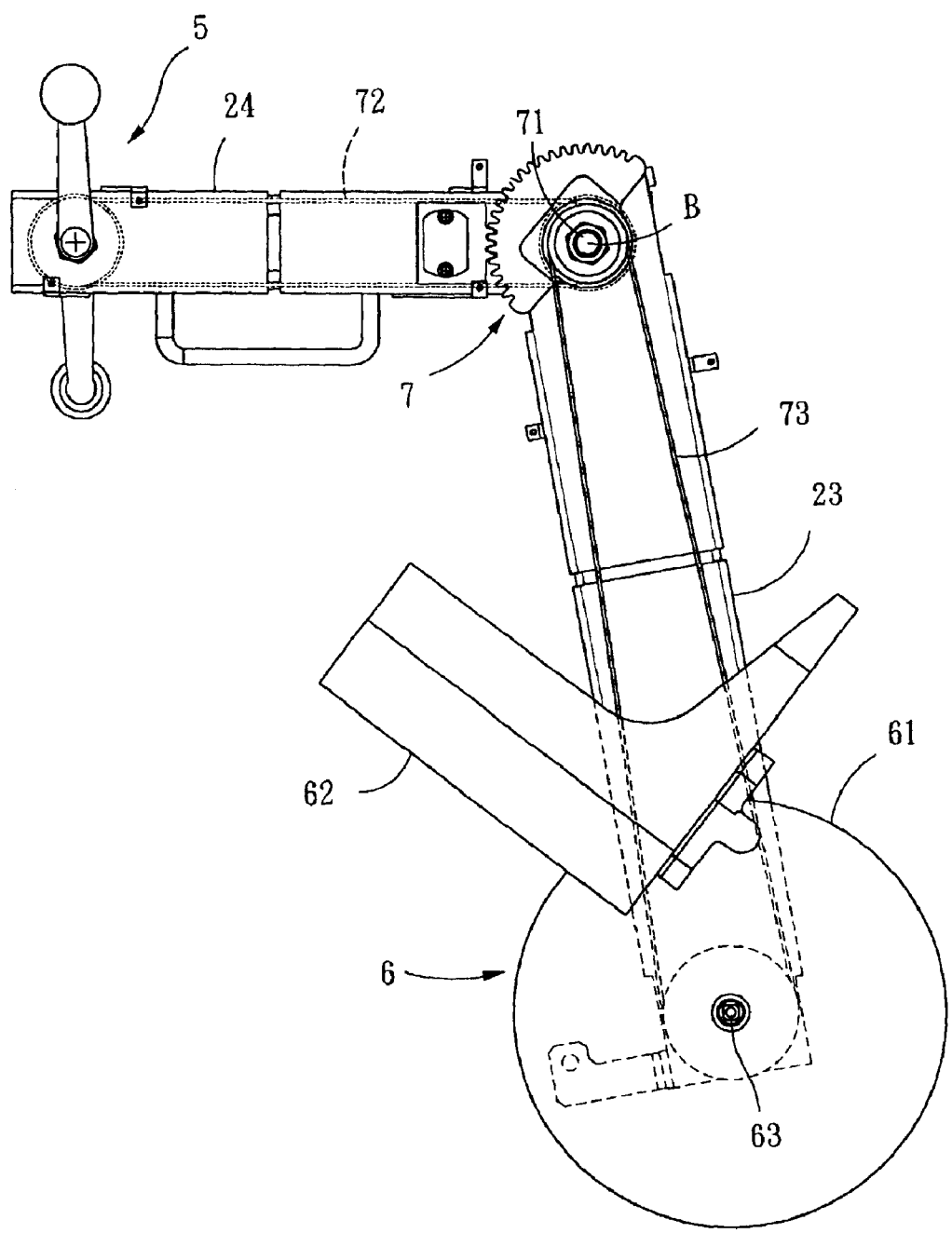
FIG. 4 is a fragmentary schematic view of the preferred embodiment to illustrate a transmission mechanism thereof.
Figure 5:
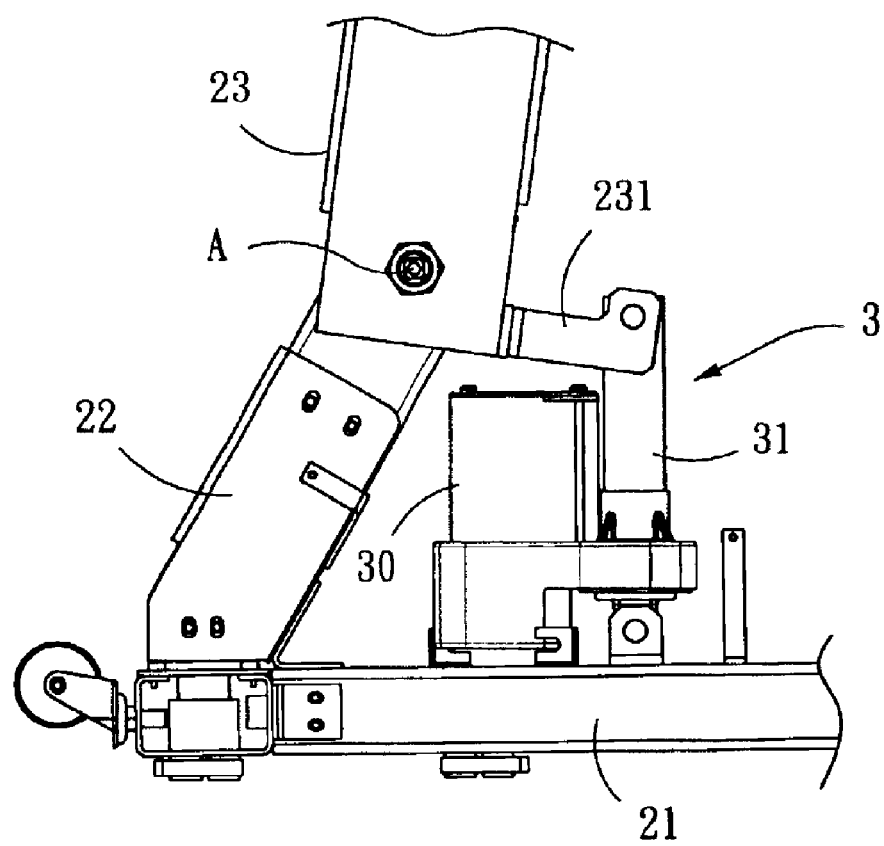
FIG. 5 is another fragmentary schematic view of the preferred embodiment to illustrate an adjustable mechanism thereof.

The post member includes first, second and third post sections 22, 23, 24. The first post section 22 has a lower end mounted on the front end of the base member 21, and an upper end opposite to the lower end of the first post section 22 in a second direction transverse to the first direction. The second post section 23 has a lower end coupled pivotally to the upper end of the first post section 22 and pivotable about a first pivot axis (A) that extends in a third direction transverse to the first and second directions, as best shown in FIG. 5. The second post section 23 further has an upper end opposite to the lower end of the second post section 23 in the second direction. The third post section 24 has a front end coupled pivotally to the upper end of the second post section 23 and pivotable about a second pivot axis (B) parallel to the first pivot axis (A), as best shown in FIG. 4. The third post section 24 further has a rear end opposite to the front end of the third post section 24 in the first direction.

In this embodiment, the rear end of the base member 21 is configured with a space that permits movement of the wheelchair 9 thereabove in the first direction toward the post member, as best shown in FIG. 2. This enables the patient on the wheelchair 9 to use the physical therapy apparatus of this invention without being transferred from the wheelchair 9.

The pedal mechanism 6 is mounted on the frame assembly 2, and includes a pair of pedal units. In this embodiment, the pedal units are respectively disposed on opposite lateral sides of the lower end of the second post section 23 and are spaced apart from each other in the third direction. In particular, the pedal mechanism 6 further includes a pedal axle 63 that is journalled on the lower end of the second post section 23. The pedal axle 63 has first and second end portions that are disposed externally and respectively on the opposite lateral sides of the second post section 23. Each of the pedal units includes a circular disc 61 and a footrest 62. The circular disc 61 is mounted to rotate with a corresponding one of the first and second end portions of the pedal axle 63. The footrest 62 is mounted eccentrically on the respective circular disc 61. More particularly, the circular disc 61 has an outer radial portion and an inner radial portion surrounded by the outer radial portion. The footrest 62 is mounted on the outer radial portion of the circular disc 61. In this embodiment, the circular disc 61 has a thickness that is reduced in radial inward directions. That is, the inner radial portion is thinner than the outer radial portion. The arrangement as such facilitates operation of the pedal mechanism 6.

The assist mechanism 5 is mounted on the frame assembly 2, and is in the form of a hand-operated crank unit. In this embodiment, the assist mechanism 5 includes a crank shaft 50 that is journalled on the rear end of the third post section 24. The crank shaft 50 has first and second end portions that are disposed externally and respectively on the opposite lateral sides of the third post section 24. The assist mechanism 5 further includes a pair of crank arms 51 connected to a respective one of the first and second end portions of the crank shaft 50 at one end for co-rotation therewith, and further connected rotatably to a respective handle 52 at the other end.

With further reference to FIG. 3, the transmission mechanism 7 is mounted on the frame assembly 2, is coupled to the pedal mechanism 6 and the assist mechanism 5 for transmitting auxiliary drive power applied through the assist mechanism 5 to the pedal mechanism 6, and includes a transmission shaft 71. In particular, the transmission shaft 71 is journalled on the front end of the third post section 24, and has first and second end portions that are disposed externally and respectively on opposite lateral sides of the third post section 24. A first transmission belt unit 72 includes a first pulley on the crank shaft 50 of the assist mechanism 5, a second pulley on the transmission shaft 71, and a transmission belt trained on the first and second pulleys. The first transmission belt unit 72 transmits auxiliary drive power applied through the assist mechanism 5 to the transmission shaft 71. A second transmission belt unit 73 includes a third pulley on the pedal axle 63 of the pedal mechanism 6, a fourth pulley on the transmission shaft 71, and a transmission belt trained on the third and fourth pulleys. The second transmission belt unit 73 transmits the auxiliary drive power from the transmission shaft 71 to the pedal mechanism 6. As such, when the user is unable to initiate or maintain operation of the pedal mechanism 6, he can operate the assist mechanism 5 to assist him in treading operation of the pedal mechanism 6.

In this embodiment, the third pulley on the pedal axle 63 is operatively associated with a unidirectional clutch device 64 (see FIG. 9) of the pedal mechanism 6 that prevents transmission of primary drive force applied through the pedal mechanism 6 to the transmission shaft 71. As such, when the user merely operates the pedal mechanism 6, the assist mechanism 5 does not rotate. This prevents the user from being injured by the assist mechanism 5. Since the feature of the present invention does not reside in the particular configuration of the clutch device, which is conventional in construction, a detailed description of the same is omitted herein for the sake of brevity.

The electrical stimulation device 8 is mounted on the frame assembly 2 and is operable in a known manner so as to generate electrical stimulus for muscle stimulation. In particular, when the patient on the wheelchair 9 places his feet on the footrests 62, the probes (not shown) of the stimulation device 8 can be placed on the lower limbs of the patient so that electrical stimulus can be applied while the patient operates the pedal mechanism 6. In this embodiment, the stimulation device 8 includes a display unit 81, which serves as an interface between the physical therapy apparatus and the user, and which displays information such as heart rate, pulse rate, number of calories burned per session, etc. Since the feature of the present invention does not reside in the particular configuration of the stimulation device 8, which is conventional in construction, a detailed description of the same is omitted herein for the sake of brevity.

Figure 1:
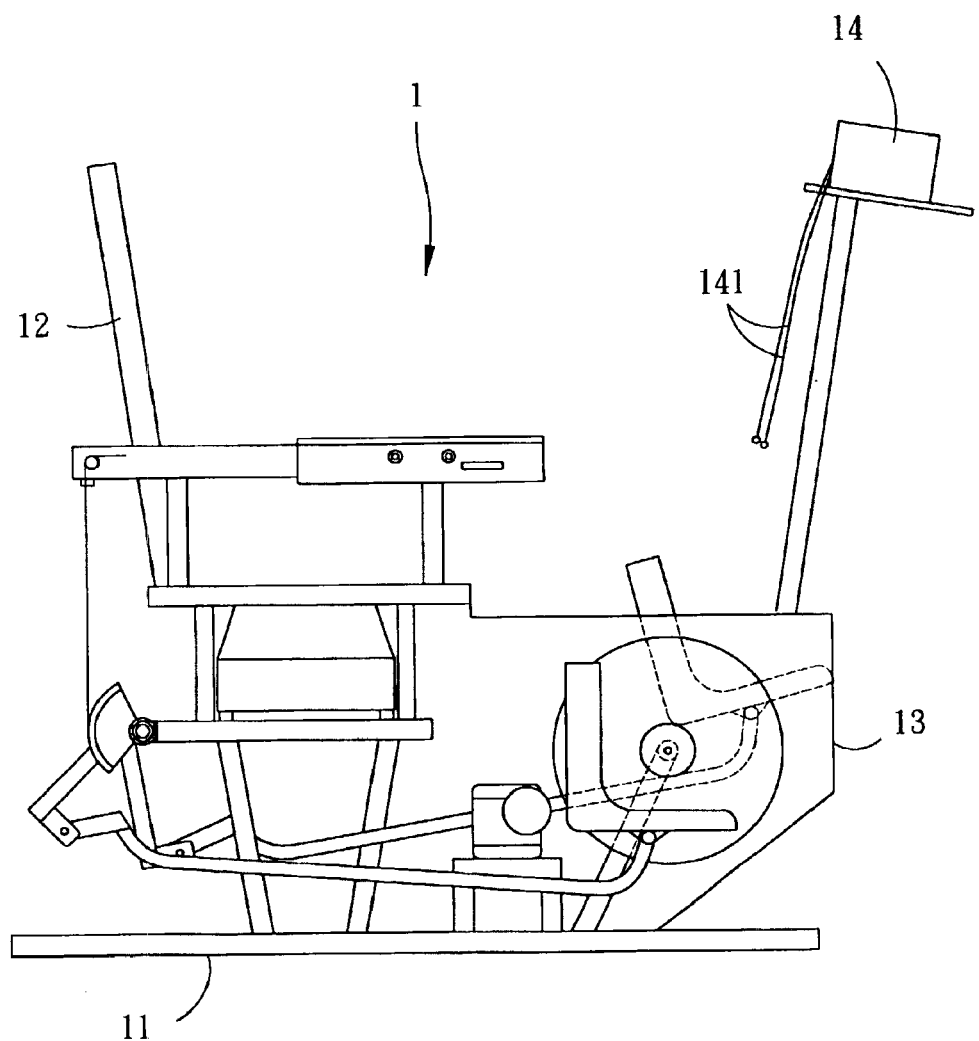
FIG. 1 is a schematic view of a conventional cycling-type physical therapy apparatus.

Referring to FIG. 5, the physical therapy apparatus further includes an adjustable mechanism 3 for adjusting inclination of the second post section 23 relative to the base member 21 so that the patient can tread on the pedal mechanism 6 (see FIG. 1) while seated on the wheelchair 9 (see FIG. 2). The lower end of the second post section 23 is formed with a rearwardly extending driven rod 231. The adjustable mechanism 3 includes a motor 30 that is mounted on the base member 21, and a drive rod 31 that has a lower rod end coupled to the motor 30 and an upper rod end connected pivotally to the driven rod 231 of the second post section 23. The motor 30 is operable so as to control vertical displacement of the drive rod 31 to retain the second post section 23 at an adjusted inclination relative to the base member 21.

Figure 6:
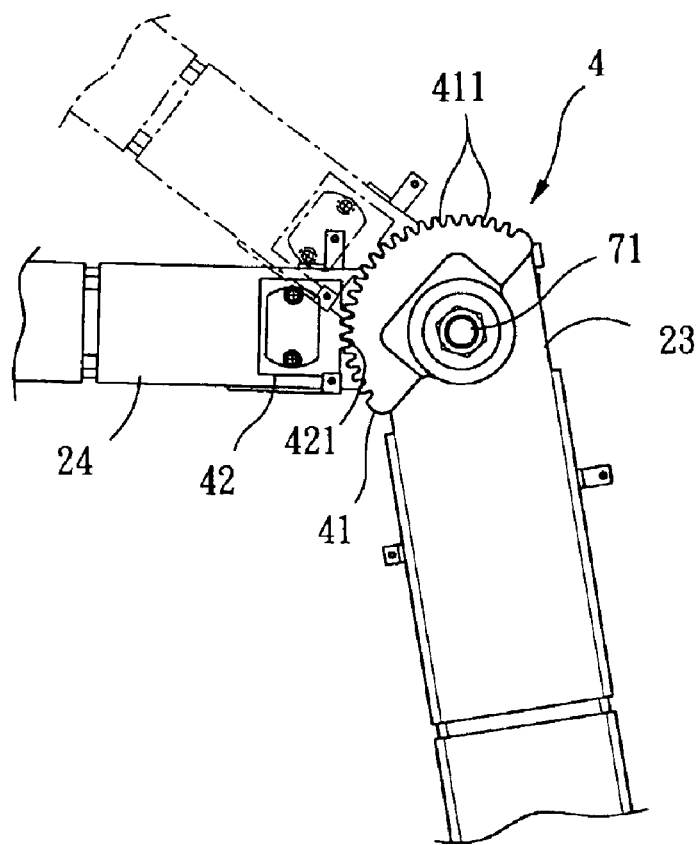
FIG. 6 is a yet another fragmentary schematic view of the preferred embodiment to illustrate a retaining mechanism thereof.
Figure 7:
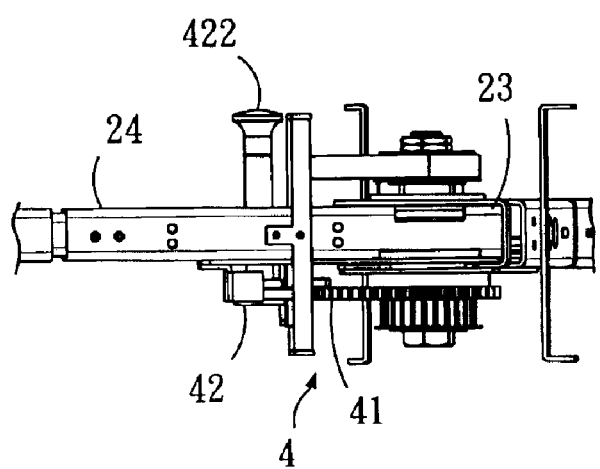
FIG. 7 is a schematic top view of FIG. 6.

Referring to FIGS. 6 and 7, the physical therapy apparatus further includes a retaining mechanism 4 for retaining the third post section 24 at a desired inclination relative to the second post section 23. In particular, the retaining mechanism 4 includes a first toothed member mounted on the second post section 23, and a second toothed member mounted on the third post section 24. The first toothed member includes a sector gear 41 that has gear teeth 411. The second toothed member includes a pawl unit 42 that has pawl teeth 421. In this embodiment, the pawl unit 42 of the second toothed member is movable toward and away from the sector gear 41 of the first toothed member to selectively engage and disengage the pawl teeth 421 of the pawl unit 42 of the second toothed member from the gear teeth 411 of the sector gear 41 of the first toothed member. The retaining mechanism 4 further includes a lever unit 422 coupled to the pawl unit 42 and operable so as to move the pawl unit 42 away from the sector gear 41, in which the inclination of the third post section 24 relative to the second post section 23 can be freely adjusted, and toward the sector gear 41, in which the third post section 24 is retained at the desired inclination relative to the second post section 23.

Figure 8:
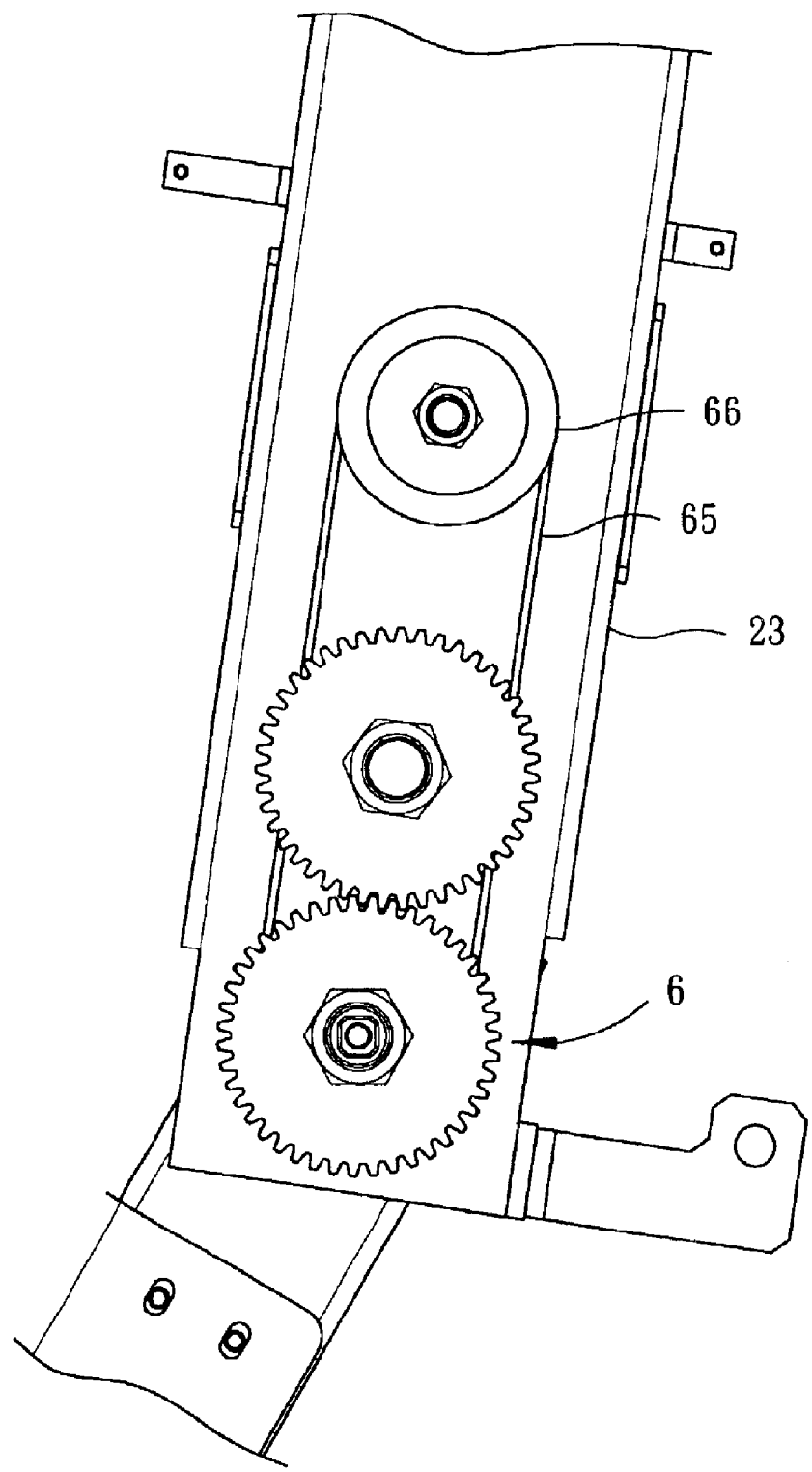
FIG. 8 is still another fragmentary schematic view of the preferred embodiment to illustrate a variable resistance device thereof.
Figure 9:
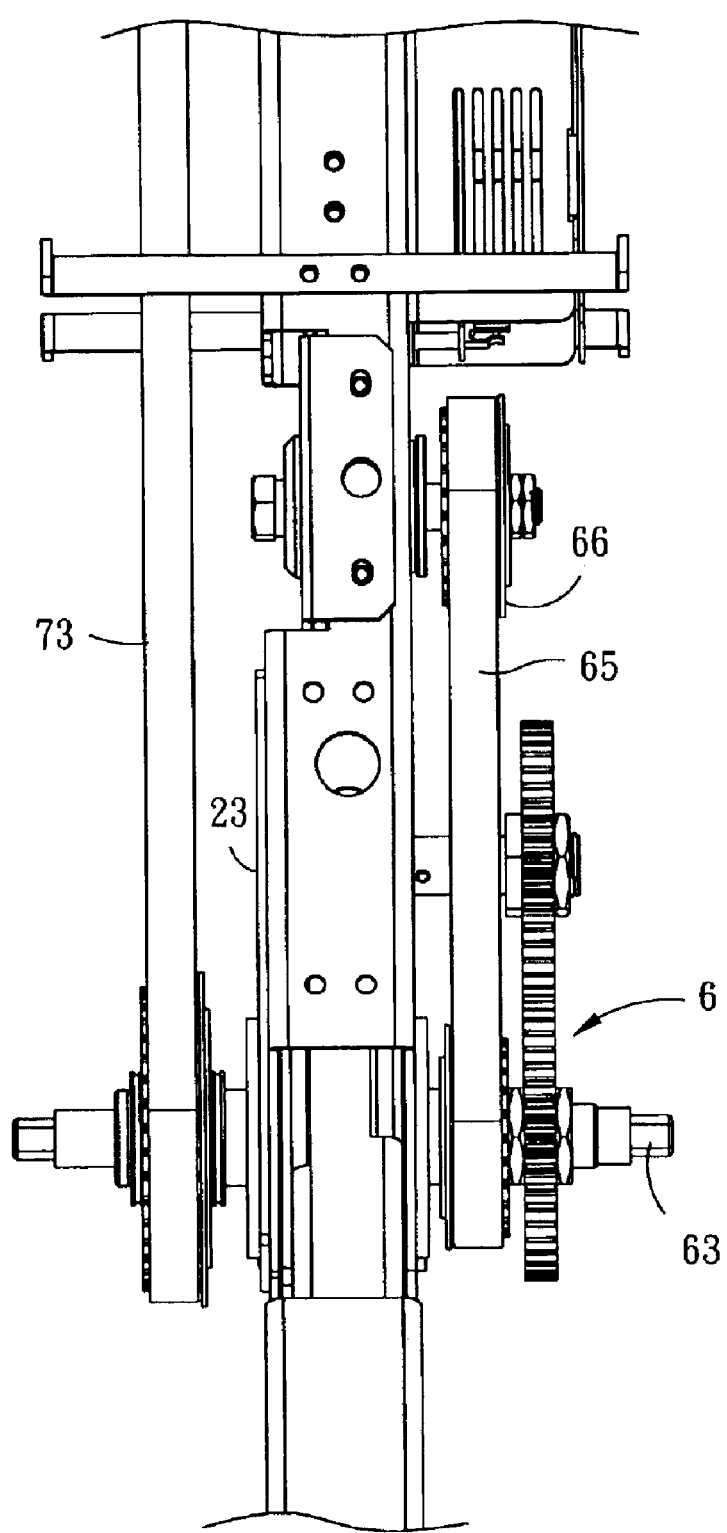
FIG. 9 is a schematic front view of FIG. 8.

Referring FIGS. 8 and 9, the physical therapy apparatus further comprises a variable resistance device 66 mounted on the frame assembly and coupled to the pedal mechanism 6 for providing a variable force to resist operation of the pedal mechanism 6. In particular, the resistance device 66 is mounted on a middle portion of the second post section 23, and is coupled to the pedal mechanism 6 by a third transmission belt unit 65. Frictional force generated by the resistance device 66 and transmitted to the pedal mechanism 6 by the third transmission belt unit 65 can be adjusted depending on the physical condition and capability of the user. Since the feature of the present invention does not reside in the particular configuration of the resistance device 66, which is conventional in construction, a detailed description of the same is omitted herein for the sake of brevity.

The first, second and third transmission belt units 72, 73, 65 of this embodiment are exemplified using timing belts. However, it should be apparent to those skilled in the art that any sort of transmission belt unit may be used as long as the intended purpose is achieved.

It has thus been shown that the physical therapy apparatus includes an adjustable mechanism 3 for adjusting inclination of the second post section 23 relative to the base member 21, and a retaining mechanism 4 for adjusting inclination of the third post section 24 relative to the second post section 23. The construction as such permits the physical therapy apparatus of this invention to accommodate users of various physical sizes. Moreover, the presence of the assist unit 5 enables continued exercising operation of the apparatus even when the user is experiencing difficulty in operating the pedal mechanism 6. Furthermore, the apparatus is designed for use while the patient remains seated on the wheelchair 9 for added convenience. The object of the invention is accordingly met.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A cycling-type physical therapy apparatus comprising:
   a frame assembly:
   a foot-operated pedal mechanism mounted on said frame assembly:
   a hand-operated assist mechanism mounted on said frame assembly:
   a transmission mechanism mounted on said frame assembly and coupled to said pedal mechanism and said assist mechanism for transmitting auxiliary drive power applied through said assist mechanism to said pedal mechanism; and an electrical stimulation device mounted on said frame assembly and operable so as to generate electrical stimulus for muscle stimulation, wherein said frame assembly includes a base member and a post member, said post member including:
   a first post section having a lower end mounted on said base member, and an upper end opposite to said lower end;
   a second post section having a lower end coupled to said upper end of said first post section, and an upper end opposite to said lower end of said second post section, said pedal mechanism being mounted on said second post section; and
   a third post section having a front end coupled to said upper end of said second post section, and a rear end opposite to said front end, said assist mechanism and said electrical stimulation device being mounted on said third post section.

2. The cycling-type physical therapy apparatus as claimed in claim 1, wherein said lower end of said second post section is coupled pivotally to said upper end of said first post section, said physical therapy apparatus further comprising an adjustable mechanism for adjusting inclination of said second post section relative to said base member.

3. The cycling-type physical therapy apparatus as claimed in claim 2, wherein said adjustable mechanism includes a motor mounted on said base member, and a drive rod having a lower rod end coupled to said motor and an upper rod end coupled to said second post section, said motor being operable so as to control vertical displacement of said drive rod to retain said second post section at an adjusted inclination relative to said base member.

4. The cycling-type physical therapy apparatus as claimed in claim 1, wherein said front end of said third post section is coupled pivotally to said upper end of said second post section, said physical therapy apparatus further comprising a retaining mechanism for retaining said third post section at a desired inclination relative to said second post section.

5. The cycling-type physical therapy apparatus as claimed in claim 4, wherein said retaining mechanism includes a first toothed member mounted on one of said second and third post sections, and a second toothed member mounted on the other of said second and third post sections and movable toward and away from said first toothed member to selectively engage and disengage said first toothed member, thereby retaining said third post section at the desired inclination relative to said second post section.

6. The cycling-type physical therapy apparatus as claimed in claim 5, wherein said first toothed member includes a sector gear, and said second toothed member includes a pawl unit for selectively engaging and disengaging said sector gear.

7. A cycling-type physical therapy apparatus comprising:
   a frame assembly:
   a foot-operated pedal mechanism mounted on said frame assembly;
   a hand-operated assist mechanism mounted on said frame assembly;
   a transmission mechanism mounted on said frame assembly and coupled to said pedal mechanism and said assist mechanism for transmitting auxiliary drive power applied through said assist mechanism to said pedal mechanism; and an electrical stimulation device mounted on said frame assembly and operable so as to generate electrical stimulus for muscle stimulation, wherein said pedal mechanism includes a pair of pedal units, each of which includes a circular disc and a footrest mounted on said circular disc, said circular disc having a thickness that is reduced in radial inward directions, said footrest being mounted eccentrically on said circular disc.

8. A cycling-type physical therapy apparatus comprising:
   a frame assembly;
   a foot-operated pedal mechanism mounted on said frame assembly;

a hand-operated assist mechanism mounted on said frame assembly;

a transmission mechanism mounted on said frame assembly and coupled to said pedal mechanism and said assist mechanism for transmitting auxiliary drive cower applied through said assist mechanism to said pedal mechanism; and an electrical stimulation device mounted on said frame assembly and operable so as to generate electrical stimulus for muscle stimulation, wherein said transmission mechanism includes a transmission shaft journalled on said frame assembly, a first transmission belt unit coupled to said assist mechanism and said transmission shaft for transmitting the auxiliary drive power applied through said assist mechanism to said transmission shaft, and a second transmission belt unit coupled to said pedal mechanism and said transmission shaft for transmitting the auxiliary drive power from said transmission shaft to said pedal mechanism.

9. The cycling-type physical therapy apparatus as claimed in claim 8, wherein said pedal mechanism includes a unidirectional clutch device that prevents transmission of primary drive force applied through said pedal mechanism to said transmission shaft.

10. A cycling-type physical therapy apparatus adapted for use by a physically impaired patient seated on a wheelchair, said physical therapy apparatus comprising:

a frame assembly including a base member and a post member, said base member having a front end and a rear end opposite to said front end in a first direction, said post member including a first post section having a lower end mounted on said front end of said base member and an upper end opposite to said lower end in a second direction transverse to the first direction, said post member further including a second post section having a lower end coupled to said upper end of said first post section and pivotable about a first pivot axis that extends in a third direction transverse to the first and second directions, said second post section further having an upper end opposite to said lower end of said second post section in the second direction a foot-operated pedal mechanism mounted on said second post section;

an adjustable mechanism for adjusting inclination of said second post section relative to said base member; and an electrical stimulation device mounted on said frame assembly and operable so as to generate electrical stimulus for muscle stimulation;

wherein said rear end of said base member is configured to permit movement of the wheelchair thereabove in the first direction toward said post member, and said adjustable mechanism permits adjustment of said second post section so that the patient can tread on said pedal mechanism while seated on the wheelchair.

11. The cycling-type physical therapy apparatus as claimed in claim 10, wherein said adjustable mechanism includes a motor mounted on said base member, and a drive rod having a lower rod end coupled to said motor and an upper rod end coupled to said second post section, said motor being operable so as to control displacement of said drive rod in the second direction to retain said second post section at an adjusted inclination relative to said base member.

12. The cycling-type physical therapy apparatus as claimed in claim 10, further comprising a hand-operated assist mechanism mounted on said frame assembly, and a transmission mechanism mounted on said frame assembly and coupled to said pedal mechanism and said assist mechanism for transmitting auxiliary drive power applied through said assist mechanism to said pedal mechanism.

13. The cycling-type physical therapy apparatus as claimed in claim 12, wherein said post member further includes a third post section having a front end coupled to said upper end of said second post section, and a rear end opposite to said front end of said third post section in the first direction, said assist mechanism and said electrical stimulation device being mounted on said third post section.

14. The cycling-type physical therapy apparatus as claimed in claim 13, wherein said front end of said third post section is pivotable about a second pivot axis parallel to the first pivot axis, said physical therapy apparatus further comprising a retaining mechanism for retaining said third post section at a desired inclination relative to said second post section.

15. The cycling-type physical therapy apparatus as claimed in claim 14, wherein said retaining mechanism includes a first toothed member mounted on one of said second and third post sections, and a second toothed member mounted on the other of said second and third post sections and movable toward and away from said first toothed member to selectively engage and disengage said first toothed member, thereby retaining said third post section at the desired inclination relative to said second post section.

16. The cycling-type physical therapy apparatus as claimed in claim 15, wherein said first toothed member includes a sector gear mounted on said second post section, and said second toothed member includes a pawl unit mounted movably on said third post section and operable so as to selectively engage and disengage said sector gear.

17. The cycling-type physical therapy apparatus as claimed in claim 12, wherein said transmission mechanism includes a transmission shaft journalled on said frame assembly, a first transmission belt unit coupled to said assist mechanism and said transmission shaft for transmitting the auxiliary drive power applied through said assist mechanism to said transmission shaft, and a second transmission belt unit coupled to said pedal mechanism and said transmission shaft for transmitting the auxiliary drive power from said transmission shaft to said pedal mechanism.

18. The cycling-type physical therapy apparatus as claimed in claim 17, wherein said pedal mechanism includes a unidirectional clutch device that prevents transmission of primary drive force applied through said pedal mechanism to said transmission shaft.

19. The cycling-type physical therapy apparatus as claimed in claim 12, wherein said hand-operated assist mechanism includes a hand-operated crank unit.

20. The cycling-type physical therapy apparatus as claimed in claim 10, wherein said pedal mechanism includes a pair of pedal units respectively disposed on opposite lateral sides of said second post section and spaced apart from each other in the third direction, each of said pedal units including a circular disc and a footrest mounted on said circular disc, said circular disc having a thickness that is reduced in radial inward directions, said footrest being mounted eccentrically on said circular disc.

21. The cycling-type physical therapy apparatus as claimed in claim 10, further comprising a variable resistance device mounted on said frame assembly and coupled to said pedal mechanism for providing a variable force to resist operation of said pedal mechanism.

* * * * *